United States Patent
Mills et al.

(10) Patent No.: US 6,682,700 B1
(45) Date of Patent: Jan. 27, 2004

(54) FREE-STANDING FLUID SENSORS, FILTERS, AND CATALYST DEVICES, AND METHODS INVOLVING SAME

(75) Inventors: Michael John Mills, Columbus, OH (US); Kenneth Henry Sandhage, Upper Arlington, OH (US); Pelagia-Irene Gouma, Columbus, OH (US)

(73) Assignee: The Ohio State University, Columbus, OH (US)

(*) Notice: Subject to any disclaimer, the term of this patent is extended or adjusted under 35 U.S.C. 154(b) by 0 days.

(21) Appl. No.: 10/114,855

(22) Filed: Apr. 2, 2002

Related U.S. Application Data

(62) Division of application No. 09/537,321, filed on Mar. 29, 2000.
(60) Provisional application No. 60/165,285, filed on Nov. 12, 1999.

(51) Int. Cl.[7] .......................... G01N 27/00; G01N 7/00; B21D 51/16; B23P 17/04
(52) U.S. Cl. ............................ 422/98; 422/90; 422/83; 29/25.01; 29/592; 29/592.1; 29/890
(58) Field of Search ............................ 422/98, 90, 83; 338/28; 29/25.01, 592, 592.1, 890

(56) References Cited

U.S. PATENT DOCUMENTS

| | | | |
|---|---|---|---|
| 4,021,326 A | 5/1977 | Pollner et al. | 204/429 |
| 4,040,930 A | 8/1977 | Dillon | 204/429 |
| 4,162,631 A * | 7/1979 | Logothetis et al. | 338/28 |
| 4,228,128 A | 10/1980 | Esper et al. | 422/98 |
| 4,270,691 A | 6/1981 | Ishii et al. | 228/194 |
| 4,953,387 A | 9/1990 | Johnson et al. | 73/25.03 |
| 5,143,696 A * | 9/1992 | Haas et al. | 422/90 |
| 5,576,067 A | 11/1996 | Miyayama et al. | 427/443.2 |
| 5,837,886 A | 11/1998 | Nakahara et al. | 73/31.06 |

FOREIGN PATENT DOCUMENTS

GB    2 067 294 A    1/1980

OTHER PUBLICATIONS

T. Y. Tien, H. L. Stadler, E. F. Gibbons, P. J. Zacminidis, $TiO_2$ as an Air–to–Fuel Sensor for Automobile Exhausts, Am. Ceram. Soc. Bull., 54, 280–282 (1975).

L. A. Harris, *A Titanium Dioxide Hydrogen Sensor*, J. Electrochem. Soc., 127, 2657–2662 (1980).

(List continued on next page.)

*Primary Examiner*—Jill Warden
*Assistant Examiner*—Brian Sines
(74) *Attorney, Agent, or Firm*—Standley & Gilcrest

(57) ABSTRACT

The present invention includes free-standing, shaped ceramic-bearing bodies useful in fluid sensors, filters, and catalyst devices. The invention also includes methods and processes for using such devices. In a preferred embodiment of the invention, shaped metallic foils are converted into free-standing, porous rutile foils having an open pore structure by oxidation at an elevated temperature. The exposure of such foils to increasing concentrations of reducing gases such as carbon monoxide results in an increase in the steady-state electrical resistance. The resultant ceramic-bearing bodies may be used as effective sensors of reducing gas species in such applications as automobile and industrial emissions. The ceramic-bearing bodies may also be used to filter out a species of a fluid, or solid particulates contained in the fluid, or catalyze reactions of a species in the fluid, such as effectively changing a harmful species like hydrocarbon gases into a relatively harmless species such as carbon dioxide and water vapor before releasing the fluid into the atmosphere, etc.

13 Claims, 2 Drawing Sheets

OTHER PUBLICATIONS

A. L. Micheli, *Fabrication and Performance Evaluation of a Titania Automotive Exhaust Gas Sensor*, Am. Ceram. Soc. Bull., 63, 694–698 (1984).

L. D. Birkefeld, A. M. Azad, and S. A. Akbar, *Carbon Monoxide and Hydrogen Detection by Anatase Modification of Titanium Dioxide*, J. Am. Ceram. Soc., 75 [11] 2964–2968 (1992).

S. R. Morrison, *Mechanism of Semiconductor Gas Sensor Operation*, Sensors and Actuators, 11, 283–287 (1987).

A. E. Jenkins, *The Oxidation of Titanium at High Temperatures in an Atmosphere of Pure Oxygen*, J. Inst. Met., 82, 213–221 (1954).

J. Stringer, *The Oxidation of Titanium in Oxygen at High Temperatures*, Acta Met., 8, 758–765 (1960).

P. Kofstad, P. B. Anderson, and O. J. Krudtaa, *Oxidation of Titanium in the Temperature Range 800–1200° C*, J. Less–Common Metals, 3, 89–97 (1961).

J. E. Lopes Gomes and A. M. Huntz, *Correlation Between the Oxidation Mechanism of Titanium Under a Pure Oxygen Atmosphere, Morphology of the Oxide Scale, and Diffusional Phenomena*, Oxid. Met., 14 [3] 249–261 (1980).

G. Bertrand, K. Jarraya, and J. M. Chaix, *Morphology of Oxide Scales Formed on Titanium*, Oxidation of Metals, 21 [1/2] 1–19 (1983).

* cited by examiner

FREE-STANDING FLUID SENSORS, FILTERS, AND CATALYST DEVICES, AND METHODS INVOLVING SAME

The present application is a divisional application of Utility application Ser. No. 09/537,321, filed Mar. 29, 2000, which claims the priority of Provisional Application Serial No. 60/165,285 filed Nov. 12, 1999, both of which are incorporated herein by reference.

TECHNICAL FIELD OF THE INVENTION

The present invention is in the field of devices and apparatus for fluid sensing, fluid filtering, and fluid catalysis.

BACKGROUND OF THE INVENTION

This invention relates to devices and methods for sensing, filtering, and catalyzing fluids. More specifically, this invention relates to oxidized metallic foils useful in such devices and methods, particularly in the automotive industry.

Recent changes in transportation regulations call for the on-board diagnosis of the performance of vehicle emissions systems. These regulations call for devices that alert a driver when the exhaust system of the driver's car is not functioning properly. Among species to be monitored are carbon monoxide (CO), hydrocarbons, and nitrogen oxides. A challenge exists to monitor the above and other species over the life of a vehicle, in a way that can survive extreme temperatures and the presence of water.

Many ceramics have found use in fluid-sensing applications, whether the fluid is a liquid or gas. For example, titania-based thick films have been demonstrated to be effective sensors of CO gas in auto and industrial emissions. Semiconducting $TiO_{2-x}$ can undergo surface reactions with a reducing gas species, such as CO, that lead to changes in resistivity proportional to the concentration of such gas species. In order to provide a large effective surface area for such reactions (i.e., for a relatively high sensitivity and rapid response), a resistance-based, titania gas sensor usually takes the form of a thin film or porous, fine-grained pellet. The ultimate success of a ceramic, however, will depend on the ability to prepare the ceramic with an appropriate pore size and structure, and maximizing the surface area of the ceramic that is capable of contacting a fluid.

It is thus an object of the present invention to develop a simple, durable, freestanding porous ceramic device capable of determining changes in concentration of select chemical species within a fluid, and similar devices to filter the fluid or catalyze a reaction with the fluid whereby any chemical species may be captured or altered by the device. It is also an object to develop methods of using such devices.

Although described with respect to the field of ceramic-based fluid sensors and the like, it will be appreciated that similar advantages may obtain in other applications of the present invention. Such advantages may become apparent to one of ordinary skill in the art in light of the present disclosure or through practice of the invention.

SUMMARY OF THE INVENTION

The present invention includes free-standing, shaped ceramic-bearing bodies useful in fluid sensors and fluid-sensing devices. The fluids may be either liquids or gases. The shaped ceramic-bearing bodies of the present invention are also useful as fluid filters and in fluid filtering devices. The shaped ceramic-bearing bodies may also be used as catalysts for reactions in contacting fluids. The present invention also includes machines and instruments using those aspects of the present invention. The invention additionally includes methods and processes for using such ceramic-bearing bodies. The methods and processes of the present invention may be applied using procedures and protocols known and used in the arts to which they pertain.

In broadest terms, the present invention includes a ceramic-based fluid sensor for sensing the change in concentration of a species in a fluid in contact therewith, comprising (1) a ceramic-bearing body fabricated from a shaped, metal-bearing precursor, the ceramic-bearing body comprising at least one ceramic phase having an open pore structure; and (2) at least two electrodes in electrical contact with the ceramic-bearing body; whereby the ceramic-bearing body is capable of undergoing a change in electrical behavior in response to a change in concentration of a species in the fluid. The ceramic-based fluid sensor may additionally have a fluid conduit in communication with the ceramic-bearing body, whereby the change in concentration of a species in the fluid passing through the fluid conduit changes the electrical behavior of the ceramic-bearing body. The change in electrical behavior, such as a change in resistivity or capacitance, may arise in changes at an interface between phases while the sensor is in contact with the fluid.

The shape of the sensor may be any predetermined shape and may be adapted to fit within the space of the fluid conduit. The predetermined shape of the ceramic-bearing sensor may be arrived at prior to oxidation of the metal-bearing precursor. The determination of appropriate shape may take into account the malleability and porosity of the metal-bearing precursor body. The metal-bearing precursor body may be shaped by any appropriate means, such as by rolling, extrusion or forging the metal-bearing precursor body into the predetermined shape or by bending a metal-bearing precursor foil over an appropriately-shaped rigid form. After oxidation, the resultant ceramic-bearing body may have substantially the same shape as the metal precursor prior to oxidation. The ceramic-bearing body may comprise a shaped, oxidized metallic foil. The metal-bearing precursor foil may be of any appropriate material, such as titanium, zirconium, hafnium, vanadium, niobium, tantalum, cerium, molybdnum, manganese, ruthenium, tin, thorium, uranium and tungsten or any combination thereof. The ceramic-bearing body may be doped with any appropriate element, such as a transition metal. The ceramic portions of the ceramic-bearing body may comprise separate layers of the body. The spacing of these layers may be controlled during the fabrication and use of the body by monitoring and appropriately modifying the surrounding conditions. The electrodes may be comprised of any appropriate material and form, such as copper, silver or gold contacts, leads wire or paste. The ceramic phase, or one of the ceramic phases, may be produced by the reaction of at least one of the aforementioned metals within the shaped precursor with one species of a fluid. The fluid species may be an atom, ion, or molecule comprised of one or more elements selected from the group consisting of oxygen, nitrogen, carbon, hydrogen, chlorine, sulfur, and combinations thereof.

Also included in the present invention is, in broadest terms, a fluid sensing device for sensing the change in concentration of a species in a fluid in contact therewith comprising: (1) a shaped, oxidized metallic foil comprising at least one ceramic phase having an open pore structure, the oxidized metallic foil containing a dopant element; (2) at least two electrodes in electrical contact with the oxidized metallic foil; and (3) a fluid conduit in communication with the oxidized metal-bearing precursor foil; whereby the doped oxidized metallic foil is capable of undergoing a change in electrical behavior in response to a change in concentration of a species in the fluid passing through the fluid conduit. The metallic foil may be of any appropriate element, such as titanium, zirconium, hafnium, vanadium, niobium, tantalum, cerium, molybdnum, manganese, ruthenium, tin, thorium, uranium and tungsten or any combination thereof. The ceramic may be doped with any appropriate dopant element as detailed above. The electrodes may be comprised of any appropriate material and form, such as copper leads, silver contacts, or gold paste. The ceramic phase, or one of the ceramic phases, may be produced by the reaction of at least one of the aforementioned metals within the shaped foil with one species of a fluid. The fluid conduit may be of any appropriate type, such as an automotive exhaust pipe, a factory smokestack, or a chemical drainpipe. The change in electrical behavior may be any detectable change, such as a change in resistivity, conductivity, or capacitance. The device measuring such change may be any appropriate device, such as an ampmeter, oscilloscope, or voltmeter.

The present invention also includes, in broadest terms, a titanium-oxide based fluid sensor for sensing the change in concentration of carbon monoxide in a fluid in contact therewith, comprising: (1) a doped titanium-oxide foil fabricated from a shaped, copper-doped titanium-bearing precursor, the foil comprising at least one ceramic phase having an open pore structure; and (2) at least two electrodes in electrical contact with the foil, such as contacts comprised of gold paste painted on the foil, whereby the doped titanium-oxide foil is capable of undergoing a change in resistivity in response to a change in concentration of carbon monoxide in the fluid. The fluid sensor may additionally have a fluid conduit in communication with the foil, whereby a change in concentration of carbon monoxide in the fluid passing through the fluid conduit affects a change in resistivity of the foil. The predetermined shape of the sensor may be such that the sensor is adapted to fit within the space of the fluid conduit.

Also included in the present invention is, in broadest terms, a fluid sensing device for sensing the change in concentration of carbon monoxide in a fluid in contact therewith comprising: (1) a shaped, titanium-oxide foil comprising at least one ceramic phase having an open pore structure, the titanium-oxide foil containing a copper dopant; (2) at least two electrodes in electrical contact with the titanium-oxide foil; and (3) a fluid conduit in communication with the titanium-oxide foil; whereby the doped titanium-oxide foil is capable of undergoing a change in resistivity in response to a change in concentration of carbon monoxide in the fluid passing through the fluid conduit. The electrodes may be comprised of any appropriate material and form, such as copper leads, silver contacts, or gold paste.

The present invention also includes, in broadest terms, a method of sensing a change in concentration of a species in a fluid, the method comprising the steps of: (1) obtaining an shaped ceramic-bearing body comprising at least one ceramic phase having an open pore structure; (2) bringing the shaped ceramic-bearing body into contact with the fluid, the fluid being capable of altering the electrical behavior of the shaped ceramic-bearing body; and (3) measuring the resultant change in the electrical behavior of said shaped ceramic-bearing body. The change in electrical behavior may relate to an alterance of any applicable, measurable characteristic, such as resistance, conductivity, or capacitance.

Also included in the present invention is, in broadest terms, a ceramic-based catalysis device for catalyzing a reaction of a species in a fluid in contact therewith comprising a ceramic-bearing body fabricated from a shaped, metal-bearing precursor, the ceramic-bearing body comprising at least one ceramic phase having an open pore structure whereby the ceramic-bearing body is capable of catalyzing a reaction in the fluid. The device may additionally have a fluid conduit in communication with the ceramic-bearing body, whereby fluid passing through the conduit undergoes a reaction catalyzed by the ceramic-bearing body. The ceramic-bearing body may be of any appropriate material listed previously, such as an oxidized metallic foil. The ceramic-bearing body may be doped with any appropriate element, such as a dopant metal selected from the group consisting of transition metals.

The present invention also includes, in broadest terms, a method of fluid catalysis comprising the steps of: (1) obtaining a shaped ceramic-bearing body comprising at least one ceramic phase having an open pore structure; and (2) bringing the shaped ceramic-bearing body into contact with a fluid, the fluid comprising at least one species capable of undergoing a reaction catalyzed by the ceramic-bearing body. The species of fluid may be any appropriate species capable of having a reaction catalyzed by a ceramic of a type described previously, such as CO or $H_2$.

Also included in the present invention is, in broadest terms, a ceramic-based fluid filter for removing at least one species of a fluid in contact therewith comprising a ceramic-bearing body fabricated from a shaped, metal-bearing precursor, the ceramic-bearing body comprising at least one ceramic phase having an open pore structure whereby the ceramic-bearing body is capable of entraining at least one species of the fluid. The filter may also have a fluid conduit in communication with the ceramic-bearing body, whereby at least one of the species of the fluid becomes entrained in the ceramic. The ceramic-bearing body may be of any appropriate material listed previously, such as an oxidized metallic foil. The ceramic-bearing body may be doped with an appropriate element, such as a dopant metal selected from the group consisting of transition metals.

Also included in the present invention is, in broadest terms, a ceramic-based fluid filter for removing at least one type of particulate from a fluid in contact therewith comprising a ceramic-bearing body fabricated from a shaped, metal-bearing precursor, the ceramic-bearing body comprising at least one ceramic phase having an open pore structure whereby the ceramic-bearing body is capable of entraining at least one type of particulate contained in the fluid. The ceramic-bearing body may entrain the particulates by either having an appropriate pore size such that the particulates become entrained in the pores, or by an electrical charge developed on the surface of the ceramic-bearing body whereby particulates may be attracted to and adhere to the surface of the ceramic-bearing body. The charge may be generated by any appropriate means, as through the accumulation of a surface static charge or through an appropriate applied voltage. The filter may also have a fluid conduit in communication with the ceramic-bearing body, whereby at least one type of solid particulate contained in the fluid becomes entrained in the ceramic-bearing body. The ceramic-bearing body may be of any appropriate material listed previously, such as an oxidized metallic foil. The ceramic-bearing body may be doped with an appropriate element, such as a dopant metal selected from the group consisting of transition metals.

The present invention also includes, in broadest terms, a method of filtering a fluid containing multiple species, the method comprising the steps of: (1) obtaining a shaped ceramic-bearing body fabricated from a shaped, metal-bearing precursor, the appropriate ceramic-bearing body comprising at least one ceramic phase having an open pore structure; and (2) bringing the shaped ceramic-bearing body into contact with the fluid, at least one of the multiple species capable of becoming entrained in the ceramic-bearing body. The species to be filtered by the fluid may be any appropriate species capable of being entrained in a ceramic-bearing body of any type described previously.

DETAILED DESCRIPTION OF THE PREFERRED EMBODIMENTS

Figure 1:
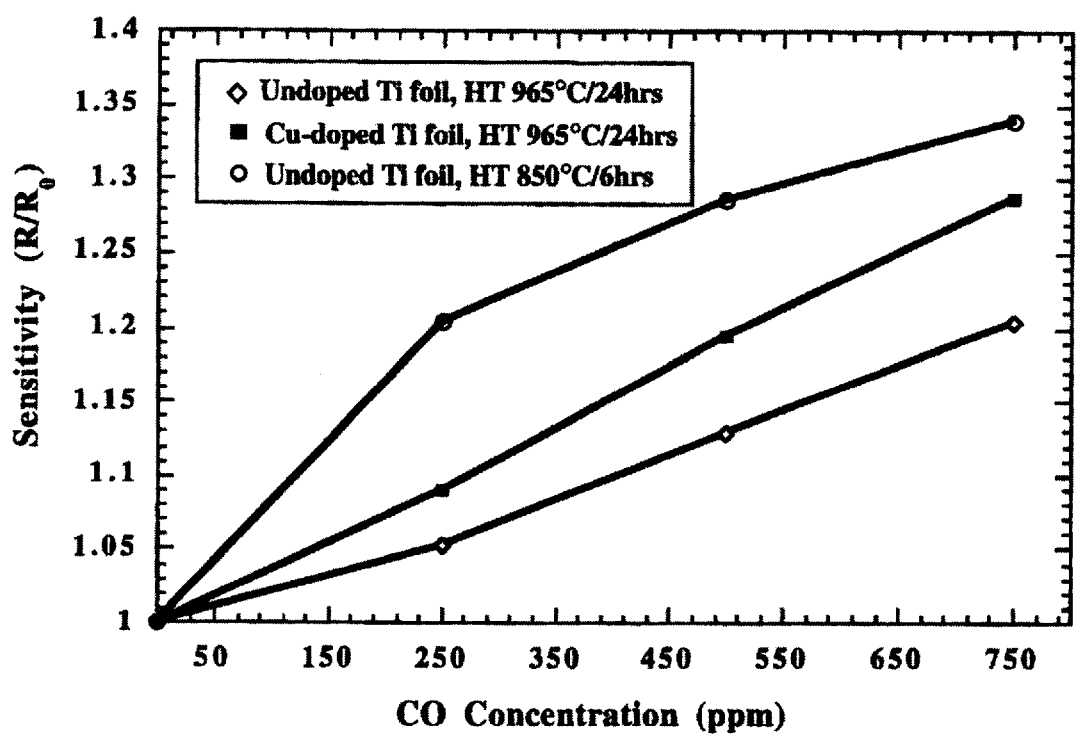
FIG. 1 is a graph showing the changes in the steady-state resistance ratio, $R/R_o$, upon exposure to various CO concentrations of oxidized specimens of the present invention.

In accordance with the foregoing summary, the following present a detailed description of a preferred embodiment of the invention that is currently considered to be the best mode.

A titanium metal foil may be used in developing a fluid sensor, filter, or catalysis device with an average thickness of 35 μm. Inductively coupled plasma mass spectroscopy may be used to first determine the presence of any major impurities. A sufficiently pure titanium foil may then be cut into pieces of appropriate dimension. The pieces may be cleaned prior to oxidation, such as by wiping the pieces with ethanol and allowing to dry. Copper particles may be deposited onto the titanium foils prior to oxidation, as Cu-doped oxidized specimens may exhibit a greater sensitivity to reducing gas species such as CO than non-doped specimens oxidized under similar conditions. The specimens may also exhibit greater sensitivity to other gases, such as methane, oxygen, or carbon dioxide. The copper deposition may be accomplished by any appropriate means, such as by sublimation, sputtering, vapor deposition, or preferably electrodeposition. If electrodeposition is to be used, the foil may preferably be immersed into a solution of 1.39 M $CuSO_4$ and 0.54 M $H_2SO_4$ with distilled water, and electrodeposition conducted using a current density of 40 mA/cm$^2$ for times ranging preferably from 10 s to 60 s. For oxidation, uncoated and copper-coated foils may be placed diagonally within an alumina combustion boat, so that both large-area surfaces of each foil will be exposed to the oxidizing atmosphere. The pieces may then be oxidized, such as may preferably be accomplished within a controlled atmosphere, horizontal tube furnace. After preferably purging the furnace with pure oxygen at room temperature, the specimens may be heated at a rate of 5° C./min to a peak temperature ranging from 800 to 965° C. and held at this temperature for 6–24 hours. The pieces may then be cooled at a rate of 10° C./min to room temperature. The foil may be bent or formed into its final state before oxidizing, and may also be placed in the sensor body prior to oxidation.

Thermogravimetric analyses may be conducted over a similar temperature range with purified, flowing oxygen to assess the oxidation kinetics. Microstructural analyses of fractured cross-sections of the oxidized specimens may also be conducted with a field emission gun scanning electron microscope. X-ray diffraction (XRD) analyses of the oxidized specimens may be conducted at room temperature using Cu-Kα radiation at a scan rate of about 1°/min. The DC resistivities of the oxidized foils may be evaluated as a function of the gas atmosphere with a multimeter using a two-point probe method. Electrical contact of the oxidized specimens to gold electrodes may be achieved by applying gold paint to the specimens and then firing the paint at about 800° C. for approximately 15 minutes in air.

The oxidized samples may then be placed within a controlled atmosphere sensing chamber and heated to 600° C. The background gas in the sensing chamber is preferably a mixture of nitrogen with 5% oxygen. A mass flow controller may be used to achieve desired CO(g) levels (preferably from 50 ppm to 750 ppm) within the sensing chamber. For any given sample, the change in steady-state resistivity upon exposure to a given CO(g) concentration may be measured with preferably at least two repetitions to ensure that the sensing performance is reproducible.

In an embodiment where the ceramic is used as a fluid sensor, such as in detecting the presence of carbon monoxide gas in automotive exhaust, the ceramic sensor may be placed inside the exhaust pipe of an automobile. It may be desirable for the ceramic to have a shape that accords with the size and contour of the inner space of an exhaust pipe. As the sensor is passed into the exhaust, the pipe acts as a fluid conduit, passing the exhaust fumes over the ceramic. An appropriate ceramic-bearing body, such as an oxidized titanium foil, may be able to detect the presence and concentration of a gas such as CO in the exhaust fumes. Detection may mean that the ceramic undergoes a change in electrical behavior, such as a change in resistance, which may be measured using any appropriate device, such as a multi-meter or any other resistance-measuring device. The change in resistance may then correspond to the concentration of the gas such as CO in the exhaust fumes.

When used as a filtering device, the ceramic may be placed into a fluid conduit, such as an industrial exhaust, which directs the fluid over the filter. One or more types of target entrappable species or particles may then be filtered out of the fluid. The device in the fluid conduit may also be of a type capable of catalyzing a reaction in the fluid, such as an embodiment where a catalysis device placed in an automotive exhaust catalyzes a reaction such as an oxidation of hydrocarbons, where the harmful hydrocarbon gas is converted to carbon dioxide and water vapor before leaving the exhaust system and entering the atmosphere.

Discussion

The initial values of temperature, time, and oxygen partial pressure chosen for titanium oxidation were based on the microstructural observations that the oxidation of titanium foils of ≧25 μm thickness at 790 to 965° C. resulted in the formation of porous scales containing a series of thin oxide layers oriented parallel to the external foil surface. An increase in the oxidation temperature at a fixed oxygen pressure resulted in a decrease in the average oxide layer thickness (from ≈6 μm at 800° C. to ≈1 μm at 965° C.) and an increase in the average separation distance between the layers (from ≈0.1 μm at 800° C. to ≈0.9 μm at 965° C.). An increase in the oxygen partial pressure from 105 torr to 570 torr at 965° C. resulted in a decrease in the average grain size of rutile crystals present within the layers. Hence, in order to form a porous titania microlaminate with relatively thin oxide layers of high surface area, initial oxidation experiments were conducted at 965° C. in pure $O_2$. See reference numbers 9 and 10.

A low-magnification secondary electron image was obtained from a fracture cross-section of a 35-micron thick titanium foil that had been exposed to oxygen for 24 h at 965° C. This heat treatment resulted in complete titanium oxidation and yielded a porous, square-shaped oxide foil with an average thickness of 62±5 μm. The oxidized foil exhibited a light yellow color and was comprised solely of rutile (confirmed by XRD analysis). Three different oxide morphologies were observed in the sample. A region comprised of porous, agglomerated oxide was located near the midplane of the oxidized foil. Near the external surfaces of the foil, the oxide possessed a higher density and larger grain size. At certain locations between these two regions, a distinct layered morphology was observed. Each layer consisted of single oxide grains joined side-by-side with occasional contact made between the grains of adjacent layers. The grains within each such layer were on the order of 0.5–1.0 μm in size, with larger grains detected at the contact points between neighboring layers. After oxidation at 965° C., the specimens were exposed to various CO(g) concentrations at 600° C. until a steady-state resistance was achieved (usually within a few minutes). The steady-state change in resistance, $R/R_O$, as a function of CO(g) concentration is shown in FIG. 1 for the 965° C./24 h specimen. The electrical resistance increased in a monotonic manner with increasing CO(g) concentration in the gas phase. The steady-state resistance for a given CO(g) concentration was found to be reproducible to within a few percent.

Cu particles were electrodeposited onto some of the Ti foil specimens prior to oxidation, in order to evaluate the effect of an acceptor dopant on the CO(g) sensing behavior of the resulting oxide foils. A BSE image was taken of the fine Cu particles dispersed on the surface of a Ti specimen after 10 s of electrodeposition (prior to oxidation). Measurement of the weight gain after electrodeposition indicated that the copper deposited on this sample accounted for 0.8% of the total specimen weight (i.e., a Cu:Ti atomic ratio of 0.006:1). After oxidation at 965° C. for 24 h, the copper-bearing samples exhibited a microstructure similar to the copper-free samples oxidized under similar conditions. Discrete particles of copper or copper oxide were not detected in specimen cross-sections. As seen in FIG. 1, the oxidized, Cu-doped specimens exhibited a greater sensitivity (i.e., larger resistance change) to CO(g) than the non-doped specimens oxidized under similar conditions.

Figure 2:
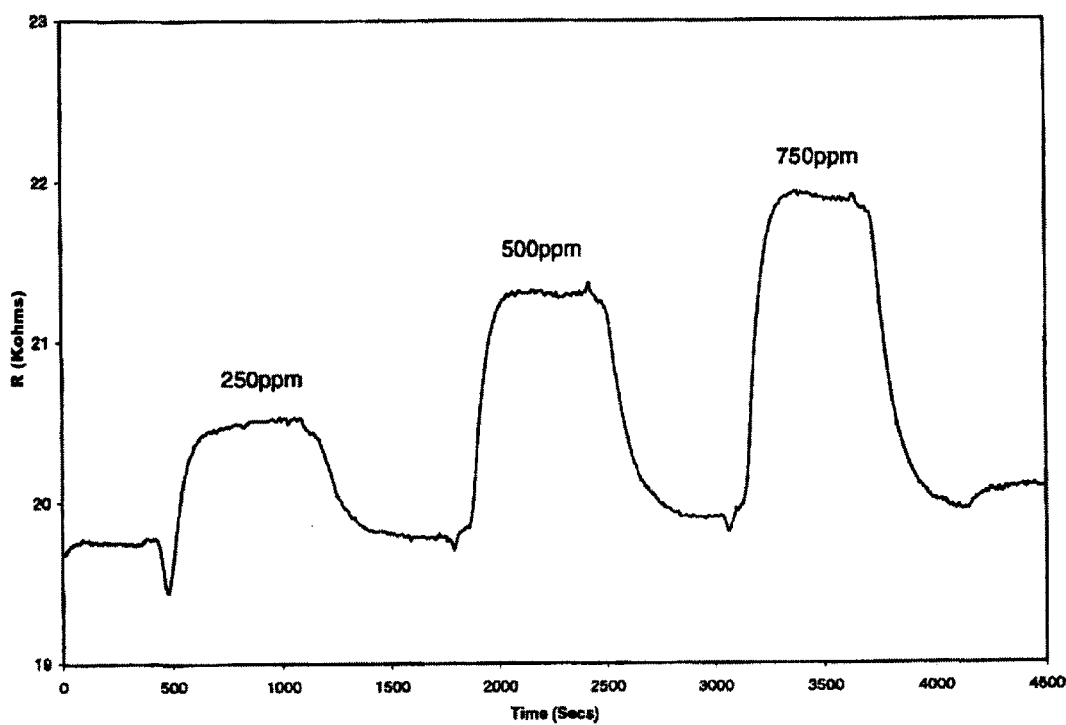
FIG. 2 is a graph showing the changes in resistance with time of exposure to various CO concentrations of oxidized specimens of the present invention.

The microlayered regions comprised a relatively small fraction of the total cross-section of the oxidized foil, which was presumably a result of post-oxidation sintering and grain growth at 965° C. In order to reduce the extent of such sintering/grain growth, subsequent oxidation experiments were conducted at lower temperatures and shorter times. TG analyses indicated that the titanium foils could be completely oxidized within 6 h at 850° C. and within 20 h at 800° C. in $O_2$. The layered oxide morphology was more prevalent in the 850° C./6 h sample than in the samples oxidized at 965° C. for 24 h. As shown in FIG. 1, the specimen oxidized at 850° C. for 6 h was more sensitive to CO(g) than the undoped specimens oxidized at 965° C. for 24 h. This difference was presumably a result of the greater exposed internal surface area (i.e., more microlayered, fine-grained oxide) within the specimen oxidized at 850° C. The time dependence of the resistance change of an 850° C./6 h specimen after exposure to various CO(g) atmospheres is shown in FIG. 2. The time required to achieve a steady-state resistance after a change was made in the CO(g) concentration was about 3 minutes. Variations in CO(g) concentration as small as 50 ppm could be detected by this sensor.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent materials or structural arrangements, or through the use of equivalent process steps, so as to be able to practice the present invention without departing from its spirit as reflected in the appended claims, the text and teaching of which are hereby incorporated by reference herein. It is the intention, therefore, to limit the invention only as indicated by the scope of the claims and equivalents thereof.

References

1. T. Y. Tien, H. L. Stadler, E. F. Gibbons, P. J. Zacminidis, $TiO_2$ as an Air-to-Fuel Sensor for Automobile Exhausts, Am. Ceram. Soc. Bull., 54, 280–282 (1975).
2. L. A. Harris, A Titanium Dioxide Hydrogen Sensor, J. Electrochem. Soc., 127, 2657–2662 (1980).
3. A. L. Micheli, Fabrication and Performance Evaluation of a Titania Automotive Exhaust Gas Sensor, Am. Ceram. Soc. Bull., 63, 694–698 (1984).
4. L. D. Birkefeld, A. M. Azad, and S. A. Akbar, Carbon Monoxide and Hydrogen Detection by Anatase Modification of Titanium Dioxide, J. Am. Ceram. Soc., 75 [11] 2964–2968 (1992).
5. S. R. Morrison, Mechanism of Semiconductor Gas Sensor Operation, Sensors and Actuators, 11, 283–287 (1987).
6. A. E. Jenkins, The Oxidation of Titanium at High Temperatures in an Atmosphere of Pure Oxygen, J. Inst. Met., 82, 213–221 (1954).
7. J. Stringer, The Oxidation of Titanium in Oxygen at High Temperatures, Acta Met., 8, 758–765 (1960).
8. P. Kofstad, P. B. Anderson, and O. J. Krudtaa, Oxidation of Titanium in the Temperature Range 800–1200° C., J. Less-Common Metals, 3, 89–97 (1961).
9. J. E. Lopes Gomes and A. M. Huntz, Correlation Between the Oxidation Mechanism of Titanium Under a Pure Oxygen Atmosphere, Morphology of the Oxide Scale, and Diffusional Phenomena, Oxid. Met., 14 [3] 249–261 (1980).
10. G. Bertrand, K. Jarraya, and J. M. Chaix, Morphology of Oxide Scales Formed on Titanium, Oxidation of Metals, 21 [1/2] 1–19 (1983).

The foregoing references are hereby incorporated herein by reference.

What is claimed is:

1. A method for making a ceramic-based sensor for sensing changes in concentration of a species in a fluid in contact therewith, said method comprising:

providing a metal precursor, said metal precursor having a shape;

processing said metal precursor so as to transform at least a portion of said metal precursor into a ceramic, wherein said ceramic has substantially the same shape as said metal precursor; and attaching at least two electrodes to said ceramic.

2. The method according to claim 1 wherein said metal precursor comprises a metal selected from the group consisting of: titanium, zirconium, hafnium, vanadium, niobium, tantalum, cerium, molybdenum, manganese, ruthenium, tin, thorium, uranium, and tungsten.

3. The method according to claim 1 wherein said metal precursor is doped with a dopant.

4. The method according to claim 3 wherein said dopant is copper.

5. The method according to claim 1 wherein said processing is accomplished by oxidation.

6. The method according to claim 1 wherein said ceramic has an open pore structure.

7. The method according to claim 1 further comprising the additional step of doping said ceramic with at least one dopant.

8. The method according to claim 7 wherein said dopant is a transition metal.

9. The method according to claim 1 wherein said ceramic undergoes a change in electrical behavior in response to a change in concentration of a species in said fluid.

10. The method according to claim 1 wherein at least one of said at least two electrodes comprises a material selected from the group consisting of copper, silver, and gold.

11. The method according to claim 1 wherein said species in said fluid comprises at least one element selected from the group consisting of oxygen, nitrogen, hydrogen, chlorine, carbon, and sulfur.

12. A ceramic-based sensor produced in accordance with the method of claim 1.

13. The method according to claim 1 wherein said ceramic has a morphology characterized by stratified layers of metal oxide.

* * * * *